(12) United States Patent
Telfort et al.

(10) Patent No.: US 11,872,156 B2
(45) Date of Patent: Jan. 16, 2024

(54) CORE BODY TEMPERATURE MEASUREMENT

(71) Applicant: Masimo Corporation, Irvine, CA (US)

(72) Inventors: Valery G. Telfort, Irvine, CA (US); Philip Perea, Irvine, CA (US); Jerome Novak, Lake Forest, CA (US)

(73) Assignee: Masimo Corporation, Irvine, CA (US)

( * ) Notice: Subject to any disclaimer, the term of this patent is extended or adjusted under 35 U.S.C. 154(b) by 1004 days.

(21) Appl. No.: 16/546,667

(22) Filed: Aug. 21, 2019

(65) Prior Publication Data

US 2020/0060869 A1 Feb. 27, 2020

Related U.S. Application Data

(60) Provisional application No. 62/810,491, filed on Feb. 26, 2019, provisional application No. 62/721,062, filed on Aug. 22, 2018.

(51) Int. Cl.
*A61F 7/02* (2006.01)
*A61B 5/01* (2006.01)
(Continued)

(52) U.S. Cl.
CPC .............. *A61F 7/02* (2013.01); *A61B 5/01* (2013.01); *A61B 5/026* (2013.01);
(Continued)

(58) Field of Classification Search
CPC ... A61B 5/01; A61B 5/026; A61B 2560/0252; A61B 2562/0271; A61F 7/02;
(Continued)

(56) References Cited

U.S. PATENT DOCUMENTS 4,960,128 A 10/1990 Gordon et al.
4,964,408 A 10/1990 Hink et al.
(Continued)

FOREIGN PATENT DOCUMENTS

CN 104 688 196 6/2015
DE 100 38 247 A1 5/2001
(Continued)

OTHER PUBLICATIONS

US 2022/0192529 A1, 06/2022, Al-Ali et al. (withdrawn)
(Continued)

*Primary Examiner* — Patrick Fernandes
*Assistant Examiner* — Anna Roberts
(74) *Attorney, Agent, or Firm* — Knobbe, Martens, Olson & Bear, LLP

(57) ABSTRACT

Continuous core body temperature measurements are made during hypothermic operations, where the core body temperature of the patient is lowered to reduce swelling. Caregivers monitor the patient's core body temperature to prevent damage that can occur to the patient if the patient's core body temperature becomes too low. To accurately determine the core body temperature of the patient, a temperature monitoring system measures the temperature at or near the surface of the patient and through at least a portion of a thermal block at multiple locations.

20 Claims, 6 Drawing Sheets

(51) Int. Cl.
   *A61B 5/026* (2006.01)
   *A61F 7/00* (2006.01)

(52) U.S. Cl.
   CPC ............... *A61B 2560/0252* (2013.01); *A61B 2562/0271* (2013.01); *A61F 2007/0001* (2013.01); *A61F 2007/0075* (2013.01); *A61F 2007/0093* (2013.01); *A61F 2007/0096* (2013.01); *A61F 2007/0288* (2013.01)

(58) Field of Classification Search
   CPC ...... A61F 2007/0001; A61F 2007/0075; A61F 2007/0093; A61F 2007/0096; A61F 2007/0288
   USPC ........................................................ 600/549
   See application file for complete search history.

(56) References Cited

U.S. PATENT DOCUMENTS

| | | |
|---|---|---|
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,685,299 A | 11/1997 | Diab et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,673 A | 9/2000 | Malin et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |

(56) References Cited

U.S. PATENT DOCUMENTS

| | | |
|---|---|---|
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,929,611 B2 | 8/2005 | Koch |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,299,090 B2 | 11/2007 | Koch |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,410,291 B2 | 8/2008 | Koch |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |

(56) References Cited

U.S. PATENT DOCUMENTS

| | | |
|---|---|---|
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,725,286 B2 | 5/2010 | Koch |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,789,554 B2 | 9/2010 | Sattler et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| 8,057,093 B2 | 11/2011 | Sattler |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,226,294 B2 | 7/2012 | Bieberich et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,292,495 B2 | 10/2012 | Bieberich et al. |
| 8,292,502 B2 | 10/2012 | Bieberich et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,511,892 B2 | 8/2013 | Koch |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |

(56) References Cited

U.S. PATENT DOCUMENTS

| | | |
|---|---|---|
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,708,926 B2 | 4/2014 | Grassl |
| 8,712,494 B1 | 4/2014 | MacNeish, III et al. |
| 8,715,206 B2 | 5/2014 | Telfort et al. |
| 8,716,629 B2 | 5/2014 | Klewer et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,272 B2 | 8/2014 | Bieberich et al. |
| 8,801,282 B2 | 8/2014 | Bieberich et al. |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,068,895 B2 | 6/2015 | Van Duren |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,101,271 B2 | 8/2015 | Sattler |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,310,257 B2 | 4/2016 | Bieberich et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,354,122 B2 | 5/2016 | Bieberich et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |

(56) References Cited

U.S. PATENT DOCUMENTS

| | | |
|---|---|---|
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,726 B2 | 11/2018 | Al-Ali et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Al-Ali et al. |
| 10,188,348 B2 | 1/2019 | Kiani et al. |
| RE47,218 E | 2/2019 | Ali-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,274,383 B2 | 4/2019 | Bieberich et al. |
| 10,278,626 B2 | 5/2019 | Schurman et al. |
| 10,278,648 B2 | 5/2019 | Al-Ali et al. |
| 10,279,247 B2 | 5/2019 | Kiani |
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B1 | 5/2019 | Poeze et al. |
| 10,299,709 B2 | 5/2019 | Perea et al. |
| 10,299,720 B2 | 5/2019 | Brown et al. |

(56) References Cited

U.S. PATENT DOCUMENTS

| | | | |
|---|---|---|---|
| 10,305,775 B2 | 5/2019 | Lamego et al. | |
| 10,307,111 B2 | 6/2019 | Muhsin et al. | |
| 10,325,681 B2 | 6/2019 | Sampath et al. | |
| 10,327,337 B2 | 6/2019 | Triman et al. | |
| 10,327,713 B2 | 6/2019 | Barker et al. | |
| 10,332,630 B2 | 6/2019 | Al-Ali | |
| 10,335,033 B2 | 7/2019 | Al-Ali | |
| 10,335,068 B2 | 7/2019 | Poeze et al. | |
| 10,335,072 B2 | 7/2019 | Al-Ali et al. | |
| 10,342,470 B2 | 7/2019 | Al-Ali et al. | |
| 10,342,487 B2 | 7/2019 | Al-Ali et al. | |
| 10,342,497 B2 | 7/2019 | Al-Ali et al. | |
| 10,349,895 B2 | 7/2019 | Telfort et al. | |
| 10,349,898 B2 | 7/2019 | Al-Ali et al. | |
| 10,354,504 B2 | 7/2019 | Kiani et al. | |
| 10,383,520 B2 | 8/2019 | Wojtczuk et al. | |
| 10,383,527 B2 | 8/2019 | Al-Ali | |
| 10,388,120 B2 | 8/2019 | Muhsin et al. | |
| D864,120 S | 10/2019 | Forrest et al. | |
| 10,441,181 B1 | 10/2019 | Telfort et al. | |
| 10,441,196 B2 | 10/2019 | Eckerbom et al. | |
| 10,448,844 B2 | 10/2019 | Al-Ali et al. | |
| 10,448,871 B2 | 10/2019 | Al-Ali et al. | |
| 10,456,038 B2 | 10/2019 | Lamego et al. | |
| 10,463,340 B2 | 11/2019 | Telfort et al. | |
| 10,471,159 B1 | 11/2019 | Lapotko et al. | |
| 10,505,311 B2 | 12/2019 | Al-Ali et al. | |
| 10,524,738 B2 | 1/2020 | Olsen | |
| 10,532,174 B2 | 1/2020 | Al-Ali | |
| 10,537,285 B2 | 1/2020 | Shreim et al. | |
| 10,542,903 B2 | 1/2020 | Al-Ali et al. | |
| 10,555,678 B2 | 2/2020 | Dalvi et al. | |
| 10,568,553 B2 | 2/2020 | O'Neil et al. | |
| 10,608,817 B2 | 3/2020 | Haider et al. | |
| D880,477 S | 4/2020 | Forrest et al. | |
| 10,617,302 B2 | 4/2020 | Al-Ali et al. | |
| 10,617,335 B2 | 4/2020 | Al-Ali et al. | |
| 10,637,181 B2 | 4/2020 | Al-Ali et al. | |
| D886,849 S | 6/2020 | Muhsin et al. | |
| D887,548 S | 6/2020 | Abdul-Hafiz et al. | |
| D887,549 S | 6/2020 | Abdul-Hafiz et al. | |
| 10,667,764 B2 | 6/2020 | Ahmed et al. | |
| D890,708 S | 7/2020 | Forrest et al. | |
| 10,721,785 B2 | 7/2020 | Al-Ali | |
| 10,736,518 B2 | 8/2020 | Al-Ali et al. | |
| 10,750,951 B1* | 8/2020 | Prachar | G01K 13/20 |
| 10,750,984 B2 | 8/2020 | Pauley et al. | |
| D897,098 S | 9/2020 | Al-Ali | |
| 10,779,098 B2 | 9/2020 | Iswanto et al. | |
| 10,827,961 B1 | 11/2020 | Iyengar et al. | |
| 10,828,007 B1 | 11/2020 | Telfort et al. | |
| 10,832,818 B2 | 11/2020 | Muhsin et al. | |
| 10,849,554 B2 | 12/2020 | Shreim et al. | |
| 10,856,750 B2 | 12/2020 | Indorf et al. | |
| D906,970 S | 1/2021 | Forrest et al. | |
| D908,213 S | 1/2021 | Abdul-Hafiz et al. | |
| 10,918,281 B2 | 2/2021 | Al-Ali et al. | |
| 10,932,705 B2 | 3/2021 | Muhsin et al. | |
| 10,932,729 B2 | 3/2021 | Kiani et al. | |
| 10,939,878 B2 | 3/2021 | Kiani et al. | |
| 10,956,950 B2 | 3/2021 | Al-Ali et al. | |
| D916,135 S | 4/2021 | Indorf et al. | |
| D917,046 S | 4/2021 | Abdul-Hafiz et al. | |
| D917,550 S | 4/2021 | Indorf et al. | |
| D917,564 S | 4/2021 | Indorf et al. | |
| D917,704 S | 4/2021 | Al-Ali et al. | |
| 10,987,066 B2 | 4/2021 | Chandran et al. | |
| 10,991,135 B2 | 4/2021 | Al-Ali et al. | |
| D919,094 S | 5/2021 | Al-Ali et al. | |
| D919,100 S | 5/2021 | Al-Ali et al. | |
| 11,006,867 B2 | 5/2021 | Al-Ali | |
| D921,202 S | 6/2021 | Al-Ali et al. | |
| 11,024,064 B2 | 6/2021 | Muhsin et al. | |
| 11,026,604 B2 | 6/2021 | Chen et al. | |
| D925,597 S | 7/2021 | Chandran et al. | |
| D927,699 S | 8/2021 | Al-Ali et al. | |
| 11,076,777 B2 | 8/2021 | Lee et al. | |
| 11,114,188 B2 | 9/2021 | Poeze et al. | |
| D933,232 S | 10/2021 | Al-Ali et al. | |
| D933,233 S | 10/2021 | Al-Ali et al. | |
| D933,234 S | 10/2021 | Al-Ali et al. | |
| 11,145,408 B2 | 10/2021 | Sampath et al. | |
| 11,147,518 B1 | 10/2021 | Al-Ali et al. | |
| 11,185,262 B2 | 11/2021 | Al-Ali et al. | |
| 11,191,484 B2 | 12/2021 | Kiani et al. | |
| D946,596 S | 3/2022 | Ahmed | |
| D946,597 S | 3/2022 | Ahmed | |
| D946,598 S | 3/2022 | Ahmed | |
| D946,617 S | 3/2022 | Ahmed | |
| 11,272,839 B2 | 3/2022 | Al-Ali et al. | |
| 11,289,199 B2 | 3/2022 | Al-Ali | |
| RE49,034 E | 4/2022 | Al-Ali | |
| 11,298,021 B2 | 4/2022 | Muhsin et al. | |
| D950,580 S | 5/2022 | Ahmed | |
| D950,599 S | 5/2022 | Ahmed | |
| D950,738 S | 5/2022 | Al-Ali et al. | |
| D957,648 S | 7/2022 | Al-Ali | |
| 11,382,567 B2 | 7/2022 | O'Brien et al. | |
| 11,389,093 B2 | 7/2022 | Triman et al. | |
| 11,406,286 B2 | 8/2022 | Al-Ali et al. | |
| 11,417,426 B2 | 8/2022 | Muhsin et al. | |
| 11,439,329 B2 | 9/2022 | Lamego | |
| 11,445,948 B2 | 9/2022 | Scruggs et al. | |
| D965,789 S | 10/2022 | Al-Ali et al. | |
| D967,433 S | 10/2022 | Al-Ali et al. | |
| 11,464,410 B2 | 10/2022 | Muhsin | |
| 11,484,265 B2 | 11/2022 | Wang et al. | |
| 11,504,058 B1 | 11/2022 | Sharma et al. | |
| 11,504,066 B1 | 11/2022 | Dalvi et al. | |
| D971,933 S | 12/2022 | Ahmed | |
| D973,072 S | 12/2022 | Ahmed | |
| D973,685 S | 12/2022 | Ahmed | |
| D973,686 S | 12/2022 | Ahmed | |
| D974,193 S | 1/2023 | Forrest et al. | |
| D979,516 S | 2/2023 | Al-Ali et al. | |
| D980,091 S | 3/2023 | Forrest et al. | |
| 11,596,363 B2 | 3/2023 | Lamego | |
| 11,627,919 B2 | 4/2023 | Kiani et al. | |
| 11,637,437 B2 | 4/2023 | Al-Ali et al. | |
| D985,498 S | 5/2023 | Al-Ali et al. | |
| 11,653,862 B2 | 5/2023 | Dalvi et al. | |
| D989,112 S | 6/2023 | Muhsin et al. | |
| D989,327 S | 6/2023 | Al-Ali et al. | |
| 11,678,829 B2 | 6/2023 | Al-Ali et al. | |
| 11,679,579 B2 | 6/2023 | Al-Ali | |
| 11,684,296 B2 | 6/2023 | Vo et al. | |
| 11,692,934 B2 | 7/2023 | Normand et al. | |
| 11,701,043 B2 | 7/2023 | Al-Ali et al. | |
| D997,365 S | 8/2023 | Hwang | |
| 11,721,105 B2 | 8/2023 | Ranasinghe et al. | |
| 11,730,379 B2 | 8/2023 | Ahmed et al. | |
| D998,625 S | 9/2023 | Indorf et al. | |
| D998,630 S | 9/2023 | Indorf et al. | |
| D998,631 S | 9/2023 | Indorf et al. | |
| 11,766,198 B2 | 9/2023 | Pauley et al. | |
| 2001/0034477 A1 | 10/2001 | Mansfield et al. | |
| 2001/0039483 A1 | 11/2001 | Brand et al. | |
| 2002/0010401 A1 | 1/2002 | Bushmakin et al. | |
| 2002/0058864 A1 | 5/2002 | Mansfield et al. | |
| 2002/0133080 A1 | 9/2002 | Apruzzese et al. | |
| 2003/0013975 A1 | 1/2003 | Kiani | |
| 2003/0018243 A1 | 1/2003 | Gerhardt et al. | |
| 2003/0144582 A1 | 7/2003 | Cohen et al. | |
| 2003/0156288 A1 | 8/2003 | Barnum et al. | |
| 2003/0212312 A1 | 11/2003 | Coffin, IV et al. | |
| 2004/0106163 A1 | 6/2004 | Workman, Jr. et al. | |
| 2005/0055276 A1 | 3/2005 | Kiani et al. | |
| 2005/0234317 A1 | 10/2005 | Kiani | |
| 2005/0245839 A1 | 11/2005 | Stivoric et al. | |
| 2006/0056487 A1* | 3/2006 | Kuroda | G01K 1/165 374/E7.042 |
| 2006/0073719 A1 | 4/2006 | Kiani | |
| 2006/0161054 A1 | 7/2006 | Reuss et al. | |
| 2006/0189871 A1 | 8/2006 | Al-Ali et al. | |

(56) References Cited

U.S. PATENT DOCUMENTS

| | | |
|---|---|---|
| 2006/0286861 A1 | 12/2006 | Avevor et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2007/0282478 A1 | 12/2007 | Al-Ali et al. |
| 2008/0033688 A1 | 2/2008 | Schermeier et al. |
| 2008/0064965 A1 | 3/2008 | Jay et al. |
| 2008/0091089 A1 | 4/2008 | Guillory et al. |
| 2008/0094228 A1 | 4/2008 | Welch et al. |
| 2008/0214949 A1 | 9/2008 | Stivoric et al. |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0063365 A1 | 3/2010 | Pisani et al. |
| 2010/0099964 A1 | 4/2010 | O'Reilly et al. |
| 2010/0113894 A1* | 5/2010 | Padiy .............. G01K 13/20 600/549 |
| 2010/0121217 A1* | 5/2010 | Padiy .............. G01K 1/16 600/549 |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0208015 A1 | 8/2011 | Welch et al. |
| 2011/0213225 A1 | 9/2011 | Bernstein et al. |
| 2011/0230733 A1 | 9/2011 | Al-Ali |
| 2011/0263950 A1 | 10/2011 | Larson et al. |
| 2012/0088999 A1 | 4/2012 | Bishay et al. |
| 2012/0123231 A1 | 5/2012 | O'Reilly |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0253334 A1 | 9/2013 | Al-Ali et al. |
| 2013/0296672 A1 | 11/2013 | O'Neil et al. |
| 2013/0296713 A1 | 11/2013 | Al-Ali et al. |
| 2013/0317388 A1 | 11/2013 | Bieberich et al. |
| 2013/0324808 A1 | 12/2013 | Al-Ali et al. |
| 2013/0331660 A1 | 12/2013 | Al-Ali et al. |
| 2013/0345921 A1 | 12/2013 | Al-Ali et al. |
| 2014/0005502 A1 | 1/2014 | Klap et al. |
| 2014/0012100 A1 | 1/2014 | Al-Ali et al. |
| 2014/0051946 A1 | 2/2014 | Arne et al. |
| 2014/0051953 A1 | 2/2014 | Lamego et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0163344 A1 | 6/2014 | Al-Ali |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0275835 A1 | 9/2014 | Lamego et al. |
| 2014/0275845 A1 | 9/2014 | Eagon et al. |
| 2014/0275871 A1 | 9/2014 | Lamego et al. |
| 2014/0275872 A1 | 9/2014 | Merritt et al. |
| 2014/0275888 A1 | 9/2014 | Wegerich et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0032029 A1 | 1/2015 | Al-Ali et al. |
| 2015/0038859 A1 | 2/2015 | Dalvi et al. |
| 2015/0055681 A1* | 2/2015 | Tsuchida .............. G01K 13/20 374/183 |
| 2015/0057562 A1 | 2/2015 | Linders et al. |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0099950 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0126822 A1 | 5/2015 | Chavan et al. |
| 2015/0165312 A1 | 6/2015 | Kiani |
| 2015/0196249 A1 | 7/2015 | Brown et al. |
| 2015/0216459 A1 | 8/2015 | Al-Ali et al. |
| 2015/0219542 A1 | 8/2015 | Kent |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257652 A1 | 9/2015 | Van Duren |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0359429 A1 | 12/2015 | Al-Ali et al. |
| 2015/0366507 A1 | 12/2015 | Blank |
| 2016/0029932 A1 | 2/2016 | Al-Ali |
| 2016/0058298 A1 | 3/2016 | Koch et al. |
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0081629 A1 | 3/2016 | Rostalski et al. |
| 2016/0095543 A1 | 4/2016 | Telfort et al. |
| 2016/0095548 A1 | 4/2016 | Al-Ali et al. |
| 2016/0095549 A1 | 4/2016 | Chang |
| 2016/0103598 A1 | 4/2016 | Al-Ali et al. |
| 2016/0166182 A1 | 6/2016 | Al-Ali et al. |
| 2016/0166183 A1 | 6/2016 | Poeze et al. |
| 2016/0183794 A1 | 6/2016 | Gannon et al. |
| 2016/0196388 A1 | 7/2016 | Lamego |
| 2016/0197436 A1 | 7/2016 | Barker et al. |
| 2016/0199576 A1 | 7/2016 | Savage |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324488 A1 | 11/2016 | Olsen |
| 2016/0327984 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0014083 A1 | 1/2017 | Diab et al. |

(56) References Cited

U.S. PATENT DOCUMENTS

| | | |
|---|---|---|
| 2017/0014084 A1 | 1/2017 | Al-Ali et al. |
| 2017/0024748 A1 | 1/2017 | Haider |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani et al. |
| 2017/0367632 A1 | 12/2017 | Al-Ali et al. |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0028072 A1 | 2/2018 | Shi |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064348 A1 | 3/2018 | Tsuchimoto |
| 2018/0064381 A1 | 3/2018 | Shakespeare et al. |
| 2018/0069776 A1 | 3/2018 | Lamego et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0216370 A1 | 8/2018 | Ishiguro et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |
| 2019/0038143 A1 | 2/2019 | Al-Ali |
| 2019/0038455 A1 | 2/2019 | Heitz et al. |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0076028 A1 | 3/2019 | Al-Ali et al. |
| 2019/0082968 A1 | 3/2019 | Karnik et al. |
| 2019/0082979 A1 | 3/2019 | Al-Ali et al. |
| 2019/0090748 A1 | 3/2019 | Al-Ali |
| 2019/0090760 A1 | 3/2019 | Kinast et al. |
| 2019/0090764 A1 | 3/2019 | Al-Ali |
| 2019/0104973 A1 | 4/2019 | Poeze et al. |
| 2019/0110719 A1 | 4/2019 | Poeze et al. |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Al-Ali |
| 2019/0122763 A1 | 4/2019 | Sampath et al. |
| 2019/0133525 A1 | 5/2019 | Al-Ali et al. |
| 2019/0142283 A1 | 5/2019 | Lamego et al. |
| 2019/0142344 A1 | 5/2019 | Telfort et al. |
| 2019/0150800 A1 | 5/2019 | Poeze et al. |
| 2019/0150856 A1 | 5/2019 | Kiani et al. |
| 2019/0167161 A1 | 6/2019 | Al-Ali et al. |
| 2019/0175019 A1 | 6/2019 | Al-Ali et al. |
| 2019/0192076 A1 | 6/2019 | McHale et al. |
| 2019/0200941 A1 | 7/2019 | Chandran et al. |
| 2019/0201623 A1 | 7/2019 | Kiani |
| 2019/0209025 A1 | 7/2019 | Al-Ali |
| 2019/0214778 A1 | 7/2019 | Scruggs et al. |
| 2019/0216319 A1 | 7/2019 | Poeze et al. |
| 2019/0216379 A1 | 7/2019 | Al-Ali et al. |
| 2019/0221966 A1 | 7/2019 | Kiani et al. |
| 2019/0223804 A1 | 7/2019 | Blank et al. |
| 2019/0231199 A1 | 8/2019 | Al-Ali et al. |
| 2019/0231241 A1 | 8/2019 | Al-Ali et al. |
| 2019/0231270 A1 | 8/2019 | Abdul-Hafiz et al. |
| 2019/0239787 A1 | 8/2019 | Pauley et al. |
| 2019/0239824 A1 | 8/2019 | Muhsin et al. |
| 2019/0320906 A1 | 10/2019 | Olsen |
| 2019/0350665 A1 | 11/2019 | Furutani et al. |
| 2019/0374713 A1 | 12/2019 | Kiani et al. |
| 2019/0388013 A1 | 12/2019 | Achmann et al. |
| 2020/0111552 A1 | 4/2020 | Ahmed |

(56) References Cited

U.S. PATENT DOCUMENTS

| | | |
|---|---|---|
| 2020/0113520 A1 | 4/2020 | Abdul-Hafiz et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2020/0390336 A1* | 12/2020 | Mensch ............. A61B 5/742 |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0186337 A1* | 6/2021 | Matsunaga ............. G01K 7/00 |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |

FOREIGN PATENT DOCUMENTS

| | | |
|---|---|---|
| DE | 100 38 247 C2 | 12/2002 |
| DE | 10 2006 012 338 B3 | 7/2007 |
| JP | 2003-322569 | 11/2003 |
| JP | 2007-296266 | 11/2007 |
| JP | 2010-000286 | 1/2010 |
| JP | 2012-237670 | 12/2012 |
| JP | 2013-526900 | 6/2013 |
| WO | WO 2009/036313 | 3/2009 |
| WO | WO 2014/047205 | 3/2014 |
| WO | WO 2014/083888 | 6/2014 |
| WO | WO 2015/172246 | 11/2015 |
| WO | WO 2016/185905 | 11/2016 |
| WO | WO 2018/152566 | 8/2018 |

OTHER PUBLICATIONS

U.S. Appl. No. 10/357,206, filed Jul. 23, 2019, Weber et al.
U.S. Appl. No. 10/357,209, filed Jul. 23, 2019, Al-Ali.
U.S. Appl. No. 10/366,787, filed Jul. 30, 2019, Sampath et al.
U.S. Appl. No. 10/368,787, filed Aug. 6, 2019, Reichgott et al.

* cited by examiner

CORE BODY TEMPERATURE MEASUREMENT

CROSS REFERENCE TO RELATED APPLICATIONS

This application claims priority to U.S. Provisional Patent Application No. 62/721,062, filed Aug. 22, 2018 and to U.S. Provisional Patent Application No. 62/810,491 filed Feb. 26, 2019, which are incorporated herein by reference in their entireties. Any and all applications, if any, for which a foreign or domestic priority claim is identified in the Application Data Sheet of the present application are hereby incorporated by reference under 37 CFR 1.57.

FIELD

The present disclosure relates generally to the field of measuring core body temperature, and in particular, to measuring core body temperature at multiple body sites to increase accuracy.

BACKGROUND

During hypothermic operations, the core body temperature of the patient is lowered to a predetermined level. Lowering the patient's core body temperature can reduce swelling of the patient during surgery and can expedite the patient's recovery time after the surgery. As the core body temperature of the patient decreases, the patient's heart rate, respiratory rate, blood pressure, and metabolic processes decrease. If the core body temperature of the patient becomes too low, the patient's cellular metabolic processes can shut down, which can lead to organ failure or death. To avoid the deleterious effects of unintentional over-cooling, the core body temperature of the patient may be constantly monitored.

SUMMARY

There is a need to provide continuous and accurate core body temperature measurements of a patient during a medical procedure during which core body temperature is intentionally reduced.

Aspects of the present disclosure are directed to accurately monitoring core body temperature. Embodiments generally include a temperature monitoring device that includes a thermal block having known dimensions and known thermal conductivity, and a first temperature measuring device coupled to the thermal block. The first temperature measuring device may be coupled to a surface of the thermal block or may be located within the thermal block. The temperature monitoring device can further include a second temperature measuring device. The second temperature measuring device may be coupled to a surface of the thermal block or may be located within the thermal block. The first and second temperature measuring devices may be located on opposing sides of the thermal block. The first and second temperature measuring devices can be located a known distance from each other on or within the thermal block.

A temperature monitoring system can include two temperature monitoring devices. The two temperature monitoring devices can be disposed at different locations on or near a patient's skin. Each temperature monitoring device can include a thermal block having known dimensions and known thermal conductivity and at least one temperature measuring device that is coupled to a surface of the thermal block or is located within the thermal block. Each temperature monitoring device can include a thermal block having known dimensions and known thermal conductivity and two temperature measuring devices. The two temperature measuring devices for each thermal block may be coupled to opposing sides of the thermal block, located within the thermal block a known distance apart, or one temperature measuring device may be located on a surface of the thermal block and the other temperature measuring device may be located within the thermal block. Each thermal block can have the same or different thermal conductivity. The temperature measuring devices can be temperature sensors, such as thermistors, resistance temperature detectors, thermocouples, semiconductor-based temperature sensors, and the like.

The temperature monitoring system can use the temperature measured by each temperature measuring device and the known thermal conductivities and dimensions of the thermal block(s) to determine the patient's core body temperature.

Temperature monitoring systems that use a single temperature monitoring device make assumptions about the thermal conductivity of the patient's skin to determine the patient's core body temperature. Assumptions about the thermal conductivity of the patient's skin can lead to errors when determining the patient's core body temperature.

Temperature monitoring systems that use at least two temperature monitoring devices can determine the patient's core body temperature without making assumptions about the thermal conductivity of the patient's skin. Because assumptions about the thermal conductivity of the patient's skin do not need to be made when at least two temperature monitoring devices are used, the temperature monitoring system having at least two temperature monitoring devices is more accurate than the temperature monitoring system having one temperature monitoring device. In addition, the temperature monitoring system that includes at least two temperature monitoring devices can also determine air temperature, such as the ambient air temperature.

Aspects of this disclosure relate to a temperature monitoring system comprising a first temperature monitoring device configured to be disposed at first location associated with a patient, where the first temperature monitoring device comprises a first temperature measuring device, a second temperature measuring device, and a first thermal block having a first thermal conductivity. At least a portion of the first thermal block can be between the first and second temperature measuring devices. The first temperature measuring device can be configured to measure a first temperature associated with the patient at the first location, and the second temperature measuring device can be configured to measure a second temperature through the at least a portion of the first thermal block.

The temperature monitoring system can further comprise a second temperature monitoring device configured to be disposed at a second location associated with the patient, where the second temperature monitoring device can comprise a third temperature measuring device, a fourth temperature measuring device, and a second thermal block having a second thermal conductivity. At least a portion of the second thermal block can be between the third and fourth temperature measuring devices. The third temperature measuring device can be configured to measure a third temperature associated with the patient at the second location, and the fourth temperature measuring device can be configured to measure a fourth temperature through the at least a portion of the second thermal block.

The temperature monitoring system can further comprise one or more processors configured to receive temperature measurements from the first, second, third, and fourth temperature measuring devices, and based on the received temperature measurements, the first and second thermal conductivities, a first distance between the first and second temperature measuring devices, and a second distance between the third and fourth temperature measuring devices, can determine a core body temperature of the patient.

The one or more processors can be further configured to determine a skin thermal resistance of the patient. The one or more processors can be further configured to determine an ambient air temperature. The first temperature measuring device can be further configured to measure the first temperature at or near a surface of the patient at the first location and the third temperature measuring device can be further configured to measure the third temperature at or near the surface of the patient at the second location. A first side of the first thermal block can be over the first location and a first side of the second thermal block can be over the second location. The second temperature measuring device can be configured to measure the second temperature at a second side opposite the first side of the first thermal block and the fourth temperature measuring device can be configured to measure the fourth temperature at a second side opposite the first side of the second thermal block. At least one of the first, second, third, and fourth temperature measuring devices can include a thermistor.

The temperature monitoring system can further comprise a display configured to display the core body temperature of the patient. The first and second distances can be approximately the same. The first and second thermal conductivities can be approximately the same. The first and second distances can also be different. The first and second thermal conductivities can also be different.

Aspects of this disclosure relate to a temperature monitoring system comprising at least two passive temperature monitoring devices configured to be disposed at respective locations associated with a patient. Each passive temperature monitoring device can comprise a thermal block between at least portions of first and second temperature measuring devices. Each first temperature measuring device can be configured to measure a temperature at the respective location. Each second temperature measurement device can be configured to measure a temperature through at least a portion of the corresponding thermal block. The temperature monitoring system can further comprise one or more processors configured to determine a core body temperature of the patient responsive to the temperature measurements and physical properties associated with the thermal blocks.

The physical properties associated with the thermal blocks can include a thermal conductivity and a thickness. For each passive temperature monitoring device, the thickness of the thermal block can represent a distance between the first and second temperature measuring devices.

Aspects of this disclosure relate to a temperature monitoring system comprising first and second temperature measuring devices, where the first temperature measuring device can be configured to be disposed at a first location associated with a patient; an insulator having a known thermal conductivity, where at least a portion of the insulator can be disposed between the first and second temperature measuring devices; and a Peltier device can be disposed over the second temperature measuring device. The temperature monitoring system can further comprise one or more processors configured to cool the insulator to a first temperature using the Peltier device; disable the Peltier device once the first temperature is reached; receive temperature measurements from the first and second temperature measuring device after disabling the Peltier device; determine a recovery time for the received temperature measurement from the first temperature measurement device to become approximately equal to the received temperature measurement from the second temperature measurement device; and determine perfusion information based at least in part on the recovery time.

The one or more processors can be further configured to determine patient care instructions based at least in part on the perfusion information. The first temperature can be approximately 2 degrees less than a temperature of the patient's skin at the first location. The first temperature can be approximately 5 degrees less than a temperature of the patient's skin at the first location. The recovery time can be based at least in part on heat flow between the first and second temperature measurement devices through the insulator.

For purposes of summarizing the disclosure, certain aspects, advantages and novel features of the innovations have been described herein. It is to be understood that not necessarily all such advantages may be achieved in accordance with any particular embodiment. Thus, the innovations may be embodied or carried out in a manner that achieves or optimizes one advantage or group of advantages as taught herein without necessarily achieving other advantages as may be taught or suggested herein.

BRIEF DESCRIPTION OF THE DRAWINGS

Various embodiments will be described hereinafter with reference to the accompanying drawings. The drawings and the associated descriptions are provided to illustrate embodiments of the present disclosure and do not limit the scope of the claims. In the drawings, similar elements have similar reference numerals.

DETAILED DESCRIPTION

Although certain embodiments and examples are described below, this disclosure extends beyond the specifically disclosed embodiments and/or uses and obvious modifications and equivalents thereof. Thus, it is intended that the scope of this disclosure should not be limited by any particular embodiments described below.

Overview of Core Temperature Measurement from Multiple Sites System

Aspects of the present disclosure describe a temperature monitoring system that measures temperature at or within thermal blocks that are disposed at multiple locations associated with a patient to determine the patient's core body temperature.

Figure 1:
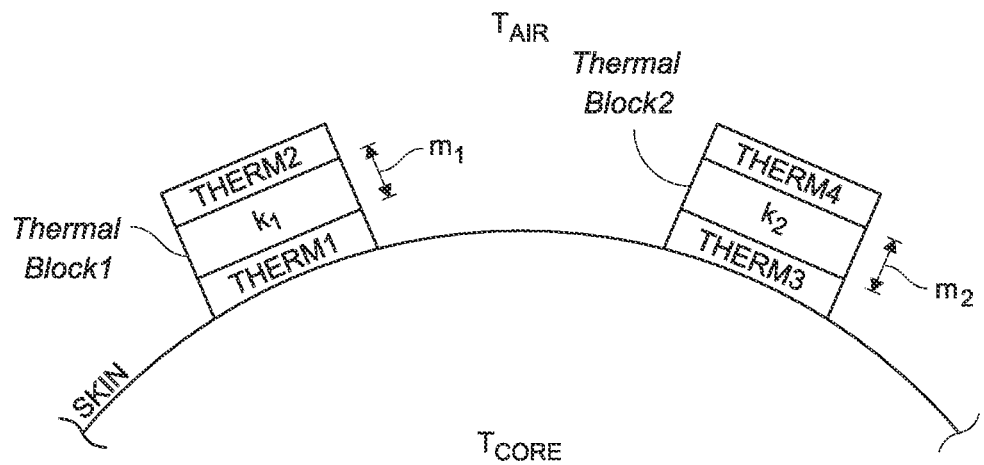
FIG. 1 is a block diagram of an example of a multi-site temperature monitoring system.
Figure 1A:
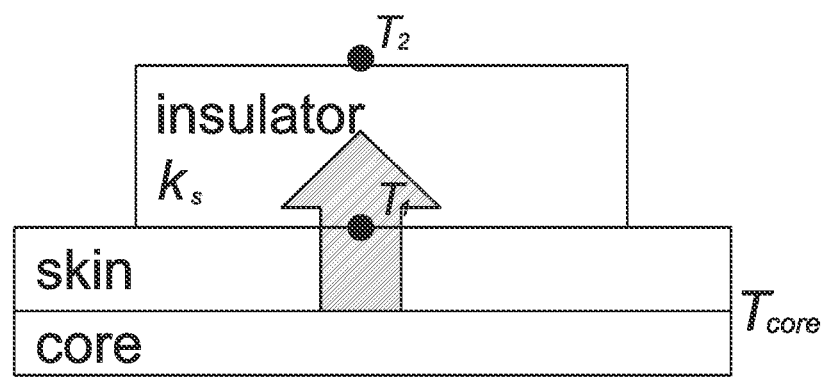
FIG. 1A is a block diagram illustrating an example of a single-site passive heat flux measurement system.

FIG. 1A is a block diagram of an example passive heat flux measurement system. In the illustrated passive heat measurement system of FIG. 1A, thermistor T1 can be positioned on top of the skin, an insulator or thermal block with a known thermal conductivity $k_s$ can be over thermistor T1, and thermistor T2 can be over the insulator. Heat flux from the skin at thermistor T1 to thermistor T2 can be measured. The temperature can calculated from the measured heat flux and the core body temperature is related to the calculated temperature. The core body temperature can be inferred from the calculated temperature. Using a single passive heat flux measurement system to infer the core body temperature based on the measured heat flux may use an estimate of the skin resistance $R_{SKIN}$. Using an estimate of the skin resistance $R_{SKIN}$ can result in an inferred core body temperature that is inaccurate or less accurate because of the estimated the skin resistance $R_{SKIN}$.

Greater accuracy for the core body temperature can be achieved by using a plurality of passive heat flux measurement systems at multiple locations on the skin of the patient. Using at least two passive heat flux measurement systems and solving at least two equations with two unknown variables, as described herein, can provide greater accuracy in the core body temperature measurement. The two unknown variables can be core body temperature and skin resistance. By using the temperature measurements from at least two passive heat flux measurement systems and the physical properties of the passive heat flux measurement systems, the core body temperature can be determined with greater accuracy because the skin resistance does not need to be estimated.

FIG. 1 is a block diagram of an example multi-site temperature monitoring system. The temperature monitoring system can comprise multiple passive heat flux measurement systems. The temperature monitoring system can include a first temperature monitoring device that can include a first thermal block (Thermal Block 1), a first temperature measuring device (THERM 1), and a second temperature measuring device (THERM 2). The temperature monitoring system can further include a second temperature monitoring device that can include a second thermal block (Thermal Block 2), a third temperature measuring device (THERM 3), and a fourth temperature measuring device (THERM 4). The patient's skin is indicated as SKIN; the patient's core body temperature is indicated as $T_{CORE}$, and the air temperature is indicated as $T_{AIR}$.

The first temperature monitoring device comprising the first temperature measuring device THERM 1, the first thermal block Thermal Block 1, and the second temperature measuring device THERM 1 can be placed at a first location associated with the surface of the patient.

For example, the first temperature measuring device THERM 1 can be placed on the patient's skin, on a covering that is on the patient's skin, or near the patient's skin at the first location associated with the patient. The first thermal block Thermal Block 1 can be placed over the first temperature measuring device THERM 1. The first temperature measuring device THERM 1 can be located within the first thermal block Thermal Block 1 at the first location. The first temperature measuring device THERM 1 can be placed on an outer surface of the first thermal block Thermal Block 1.

The second temperature measuring device THERM 2 can be placed over the first thermal block Thermal Block 1. The second temperature measuring device THERM 2 can be located within the first thermal block Thermal Block 1 at the first location and separated from the first temperature measuring device THERM 1 by a known distance. The second temperature measuring device THERM 2 can be located on an outer surface of the first thermal block Thermal Block 1. The outer surface of the first thermal block Thermal Block 1 associated with the second temperature measuring device THERM 2 may be opposed to an outer surface of the first thermal block Thermal Block 1 associated with the first temperature measuring device THERM 1.

The second temperature monitoring device comprising the third temperature measuring device THERM 3, the second thermal block Thermal Block 2, and the fourth temperature measuring device THERM 4 can be placed at a second location associated with the surface of the patient.

For example, the third temperature measuring device THERM 3 can be placed on the patient's skin, on a covering that is on the patient's skin, or near the patient's skin at a second location, different from the first location, and associated with the patient. The second thermal block Thermal Block 2 can be placed over the third temperature measuring device THERM 3. The third temperature measuring device THERM 3 can be located within the second thermal block Thermal Block 2 at the second location. The third temperature measuring device THERM 3 can be placed on an outer surface of the second thermal block Thermal Block 2.

The fourth temperature measuring device THERM 4 can be placed over the second thermal block Thermal Block 2. The fourth temperature measuring device THERM 4 can be located within the second thermal block Thermal Block 2 at the second location and separated from the third temperature measuring device THERM 3 by a known distance. The fourth temperature measuring device THERM 4 can be located on an outer surface of the second thermal block Thermal Block 2. The outer surface of the second thermal block Thermal Block 2 associated with the fourth temperature measuring device THERM 4 may be opposed to an outer surface of the second thermal block Thermal Block 2 associated with the third temperature measuring device THERM 3.

The temperature measuring devices THERM 1, THERM 2, THERM 3, THERM 4 are shown as blocks having height and width for illustrative purposes. The one or more of the temperature measuring devices THERM 1, THERM 2, THERM 3, THERM 4 may be a small device in relation to the thermal blocks Thermal Block 1, Thermal Block 2, and occupy a point or small area on or over the patient's skin or within the thermal blocks Thermal Block 1, Thermal Block 2.

The thermal blocks Thermal Block 1, Thermal Block 2 are shown as rectangles having height and width for illustrative purposes. One or more of the thermal blocks Thermal Block 1, Thermal Block 2 may be cubic, cylindrical, spherical, irregularly-shaped, and the like.

The first and second temperature measuring devices THERM 1, THERM 2 are separated by a distance $m_1$ of the first thermal block Thermal Block 1 and the third and fourth temperature measuring devices THERM 3, THERM 4 are separated by a distance $m_2$ of the second thermal block Thermal Block 2. In some embodiments, $m_1$ and $m_2$ can be substantially the same. In alternative embodiments, $m_1$ and $m_2$ can be different.

The first thermal block Thermal Block 1 can have a thermal conductivity $k_1$ and the second thermal block Thermal Block 2 can have a thermal conductivity $k_2$. Thermal conductivity can include the degree to which a specific material conducts heat. Thermal conductivity can be expressed in units of W/m° K. The first and second thermal blocks THERM 1 and THERM 2 can be the same material, such that $k_1$ and $k_2$ are substantially the same. In alternative embodiments, the first and second thermal blocks THERM 1 and THERM 2 can be different materials, such that $k_1$ and $k_2$ are different. One or more of the thermal blocks THERM 1, THERM 2 can comprise multiple materials such that $k_1$ and $k_2$ are not constant but are functions of the thicknesses of the multiple materials.

The first temperature measuring device THERM 1 can measure the temperature associated with the surface of the patient, such as at or near the patient's skin, at the first location, and the second temperature measuring device THERM 2 can measure the temperature through the first thermal block Thermal Block 1 at a distance $m_1$ from the first temperature measuring device THERM 1 at the first location.

The third temperature measuring device THERM 3 can measure the temperature associated with the surface of the patient, such as at or near the patient's skin, at the second location, and the fourth temperature measuring device THERM 4 can measure the temperature through the second thermal block Thermal Block 2 at a distance $m_2$ from the third temperature measuring device THERM 3 at the second location.

Examples of temperature measuring devices are, but not limited to, temperature sensors, resistance temperature detector, a thermocouple, semiconductor-based sensors, infrared sensors, bimetallic devices, thermometers, thermistors, change-of-state sensors, silicon diodes, and/or the like.

The temperature monitoring system of FIG. 1 illustrates two temperature monitoring devices. In some embodiments, the temperature monitoring system can include more than two temperature monitoring devices.

Instrumentation-Sensors and Signal Processing Device

Figure 2:
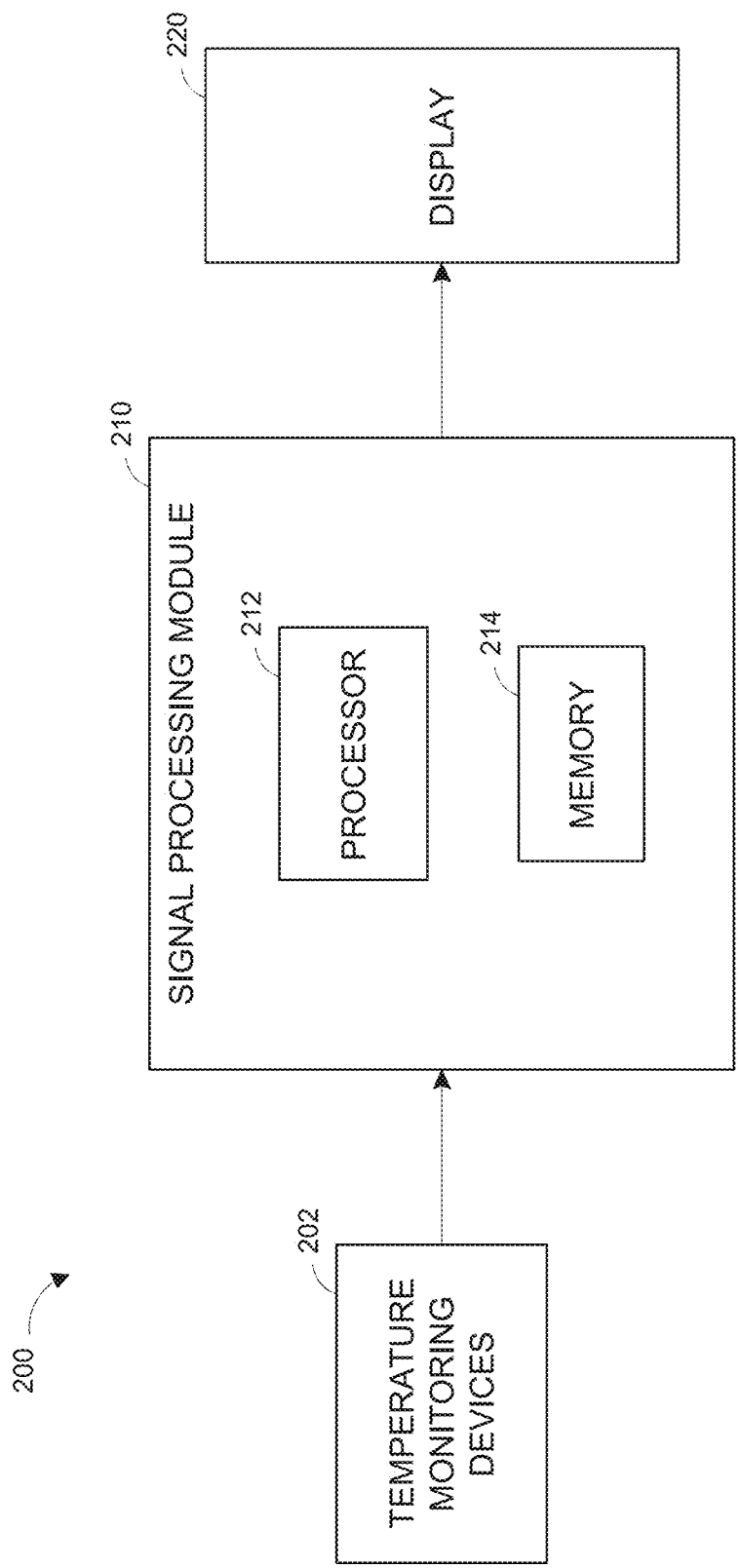
FIG. 2 is a block diagram of an example of a multi-site temperature monitoring system.

FIG. 2 is a block diagram of an example multi-site temperature monitoring system 200 according. The multi-site temperature monitoring system 200 can include one or more temperature monitoring devices 202, a signal processing module 210, and a display 220. The signal processing module 210 can include a processor 212 and a memory 214. The one or more temperature monitoring devices 202 each can include at least one temperature measuring device and a thermal block. The temperature monitoring devices 202, the signal processing module 210, and/or the display 220 can be connected via a cable or cables, wireless technology, Bluetooth®, and can communicate using near field communication protocols, Wi-Fi, and/or the like.

The temperature measurements from the temperature monitoring devices 202 can be received by the signal processing module 210 and stored in memory 214. The temperature monitoring devices 202 can transmit raw sensor data to the signal processing module 210, and the signal processing module 210 can convert the raw sensor data into data representing physiological parameters for transmission to the display 220. For example, temperature measurements can be analyzed by the processor 212 to estimate a patient's core body temperature. The processor 212 can transmit the estimated core body temperature to the display 220 to be displayed.

Figure 3:
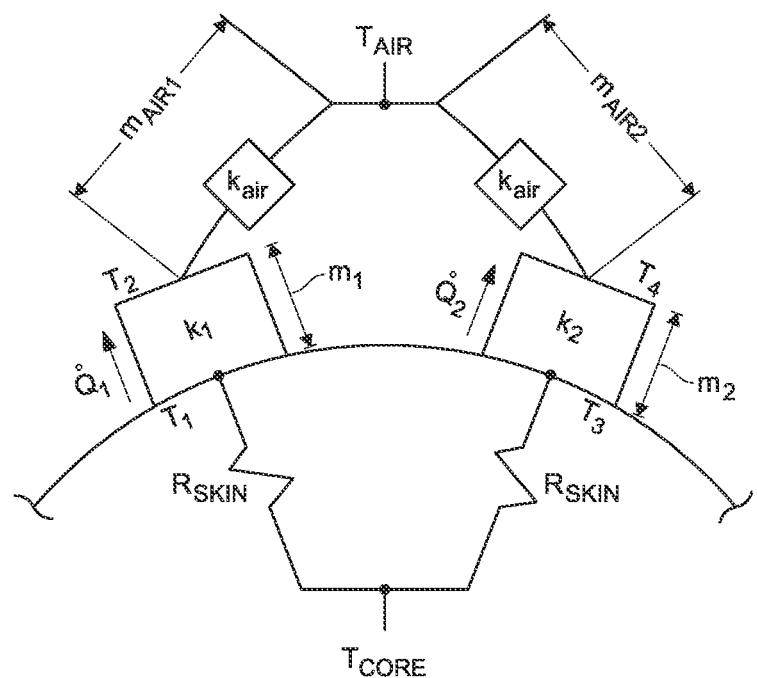
FIG. 3 is a circuit block diagram representation of an example a multi-site temperature monitoring system.

Circuit Block Diagram Representation of Multi-Site Core Temperature Monitoring System FIG. 3 is a circuit block diagram representation of an example multi-site temperature monitoring system. The temperature monitoring system can include a first temperature monitoring device that can include a first thermal block having a thermal conductivity $k_1$, a first temperature measuring device that can measure a first temperature $T_1$ and a second temperature measuring device that can measure a second temperature $T_2$. The temperature monitoring system can further include a second temperature measuring device that can include a second thermal block having a thermal conductivity $k_2$, a third temperature measuring device that can measure a third temperature $T_3$ and a fourth temperature measuring device that can measure a fourth temperature $T_4$.

The thermal conductivities $k_1$ and $k_2$ can be substantially the same. In alternative embodiments, the thermal conductivities $k_1$ and $k_2$ can be different. The two thermal blocks of FIG. 3 can include the first thermal block Thermal Block 1 and second thermal block Thermal Block 2 as illustrated in FIG. 1. The temperatures $T_1$, $T_2$, $T_3$, $T_4$ can be measured by the first, second, third, and fourth temperature measuring devices THERM 1, THERM 2, THERM 3, THERM 4, respectively, as illustrated in FIG. 1.

The distance $m_1$ is the distance between the first and second temperature measuring devices through the first thermal block and the distance $m_2$ is the distance between the third and fourth temperature measuring devices through the second thermal block. The distances $m_1$ and $m_2$ can be substantially the same. In alternative embodiments, the distances $m_1$ and $m_2$ can be different.

FIG. 3 also illustrates the thermal conductivity of air $k_{air}$, the air temperature $T_{AIR}$, the patient's core body temperature $T_{CORE}$, and the thermal resistance of the patient's skin $R_{SKIN}$. Thermal resistance can be an indication of a material's resistance to heat flow. Thermal resistance can be expressed in units of ° K/W. FIG. 3 illustrates two distances, $m_{AIR1}$ and $m_{AIR2}$, between a location on or within each thermal block, respectively, and a location in the air, indicated by $T_{AIR}$.

The temperature monitoring system of FIG. 3 illustrates heat transfer rates, $\dot{Q}_1$ and $\dot{Q}_2$, associated with the first and second thermal blocks, respectively. Heat transfer rates can include the rate at which the heat is transferred through a material. Heat transfer rates can be expressed in units of Watts. The heat transfer rates, $\dot{Q}_1$ and $\dot{Q}_2$, can indicate the heat transferred through the thermal blocks over a time interval.

The first temperature monitoring device and the second temperature monitoring device can be placed at different locations associated with the surface of the patient. For example, the first temperature monitoring device and the second temperature monitoring device can be placed at different locations on or near the patient's skin. The embodiment of the circuit block diagram in FIG. 3 illustrates two temperature monitoring devices. The multi-site core temperature monitoring system can include more than two temperature monitoring devices disposed on different locations associated with the surface of the patient. For example, the multi-site core temperature monitoring system can include three, four, five, more than five, six, etc. temperature monitoring devices disposed on different locations associated with the surface of the patient.

Circuit Representation of Multi-Site Core Temperature Monitoring System

Figure 4:
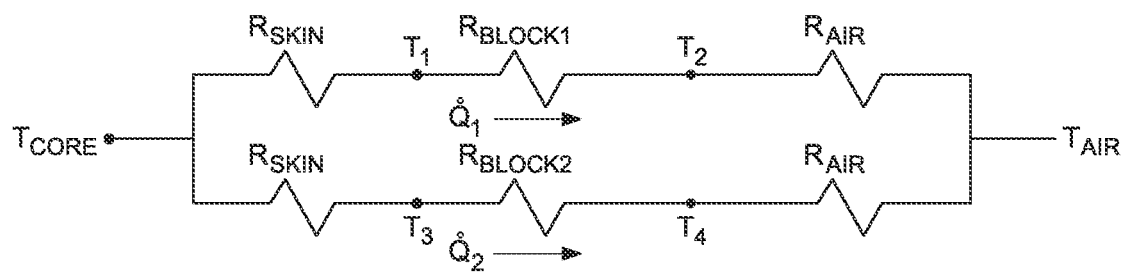
FIG. 4 is a circuit representation of an example multi-site temperature monitoring system.

FIG. 4 is a circuit representation of the example multi-site core body temperature monitoring system illustrated in FIGS. 1 and 3. The circuit representation can include the patient's core body temperature $T_{CORE}$, the thermal resistance of the patient's skin $R_{SKIN}$, a thermal resistance of the first thermal block $R_{BLOCK1}$, a thermal resistance of the second thermal block $R_{BLOCK2}$, a thermal resistance of the air $R_{AIR}$, temperatures $T_1$, $T_2$, $T_3$, and $T_4$, the heat transfer rate $\dot{Q}_1$ associated with the heat transfer of the first thermal block, the heat transfer rate $\dot{Q}_2$ associated with the heat transfer of the second thermal block, and the air temperature $T_{AIR}$.

Equations based on the circuit representation can be used to determine the core body temperature $T_{CORE}$ of the patient. The equations and calculations below illustrate one possible example that can be used to determine the core body temperature $T_{CORE}$ of the patient using the measured temperatures $T_1$, $T_2$, $T_3$, and $T_4$, the known thermal conductivities $k_1$, $k_2$ of the first and second thermal blocks, respectively, and the distances $m_1$ and $m_2$ between the first and second temperature measuring devices and the third and fourth temperature measuring devices, respectively. In other embodiments, other calculations and equations can be used to determine the core body temperature $T_{CORE}$ of the patient based on the temperature monitoring systems of FIGS. 1-4.

The thermal resistance $R_{BLOCK1}$ and $R_{BLOCK2}$ can be determined by:

$$R_{BLOCK1} = \frac{1}{k_1 m_1}$$

$$R_{BLOCK2} = \frac{1}{k_2 m_2}$$

where:
$k_1$ is the thermal conductivity of the first thermal block Thermal Block 1;
$k_2$ is the thermal conductivity of the second thermal block Thermal Block 2;
$m_1$ is the distance through the first thermal block Thermal Block 1 between the first temperature measuring device THERM 1 and the second temperature measuring device THERM 2; and
$m_2$ is the distance through the second thermal block Thermal Block 2 between the third temperature measuring device THERM 3 and the fourth temperature measuring device THERM 4.

The heat transfer rates, $\dot{Q}_1$ and $\dot{Q}_2$, for each of the two thermal blocks can be determined by:

$$\dot{Q}_1 = \frac{T_2 - T_1}{R_{BLOCK1}}$$

$$\dot{Q}_2 = \frac{T_4 - T_3}{R_{BLOCK2}}$$

where:
$T_1$ is the temperature measured by the first temperature measuring device THERM 1;
$T_2$ is the temperature measured by the second temperature measuring device THERM 2;
$T_3$ is the temperature measured by the third temperature measuring device THERM 3; and
$T_4$ is the temperature measured by the fourth temperature measuring device THERM 4.

The core body temperature of the patient $T_{core}$ can be determined by:

$$T_{CORE} - T_1 = \dot{Q}_1 R_{SKIN}$$

$$T_{CORE} - T_3 = \dot{Q}_2 R_{SKIN}$$

where $R_{SKIN}$ represents the thermal resistance of the patient's skin.

With two equations for the core temperature and two unknowns ($T_{CORE}$ and $R_{SKIN}$), each value can be determined. An example calculation is:

$$T_{CORE} = (\dot{Q}_2 R_{SKIN}) + T_3$$

$$(\dot{Q}_2 R_{SKIN}) + T_3 - T_1 = \dot{Q}_1 R_{SKIN}$$

$$(\dot{Q}_2 R_{SKIN}) - (\dot{Q}_1 R_{SKIN}) = T_1 - T_3$$

$$R_{SKIN}(\dot{Q}_2 - \dot{Q}_1) = T_1 - T_3$$

$$R_{SKIN} = \frac{T_1 - T_3}{\dot{Q}_2 - \dot{Q}_1}$$

$$T_{CORE} = \dot{Q}_1 R_{SKIN} + T_1$$

$$T_{CORE} = \dot{Q}_1 \left(\frac{T_1 - T_3}{\dot{Q}_2 - \dot{Q}_1}\right) + T_1$$

where, as shown above:

$$\dot{Q}_1 = \frac{T_2 - T_1}{R_{BLOCK1}};$$

$$R_{BLOCK1} = \frac{1}{k_1 m_1};$$

$$\dot{Q}_2 = \frac{T_4 - T_3}{R_{BLOCK2}}; \text{ and}$$

$$R_{BLOCK2} = \frac{1}{k_2 m_2}.$$

Further, equations based on the circuit representation can be used to determine the temperature of the air $T_{AIR}$. In some embodiments, $T_{AIR}$ represents the ambient air temperature. The equations and calculations below illustrate one possible example that can be used to solve for the temperature of the air $T_{AIR}$ using the measured temperatures $T_1$, $T_2$, $T_3$, and $T_4$, the known thermal conductivities $k_1$, $k_2$ of the first and second thermal blocks, respectively, and the distances $m_1$ and $m_2$ between the first and second temperature measuring devices and the third and fourth temperature measuring devices, respectively. In other embodiments, other calculations and equations can be used to determine the air temperature $T_{AIR}$ based on the temperature monitoring systems of FIGS. 1-4.

The temperature of the air $T_{AIR}$ can be determined by:

$$T_{AIR} - T_2 = \dot{Q}_1 R_{AIR}$$

$$T_{AIR} - T_4 = \dot{Q}_2 R_{AIR}$$

where:
$R_{AIR}$ represents the thermal resistance of air;
$T_2$ is the temperature measured by the second temperature measuring device THERM 2;
$T_4$ is the temperature measured by the fourth temperature measuring device THERM 4;

$$\dot{Q}_1 = \frac{T_2 - T_1}{R_{BLOCK1}};$$

$$R_{BLOCK1} = \frac{1}{k_1 m_1};$$

$$\dot{Q}_2 = \frac{T_4 - T_3}{R_{BLOCK2}}; \text{ and}$$

$$R_{BLOCK2} = \frac{1}{k_2 m_2}.$$

With two equations for the air temperature and two unknowns ($T_{AIR}$ and $R_{AIR}$), each value can be determined. For example, the values of $T_{AIR}$ and $R_{AIR}$ can be determined in a similar manner as described above with respect to $T_{CORE}$ and $R_{SKIN}$. In an aspect, the ambient temperature calculation can improve or refine the core body temperature calculation. The ambient temperature calculation can provide patient thermoregulation information. For example, the ambient temperature calculation may be useful in determining whether the patient is under thick insulation (i.e., a thick blanker), has little insulation (i.e., a shirt and no blanket), or has no insulation (patient's skin exposed to air).

Flow Diagram for Multi-Site Core Temperature Monitoring System

Figure 5:
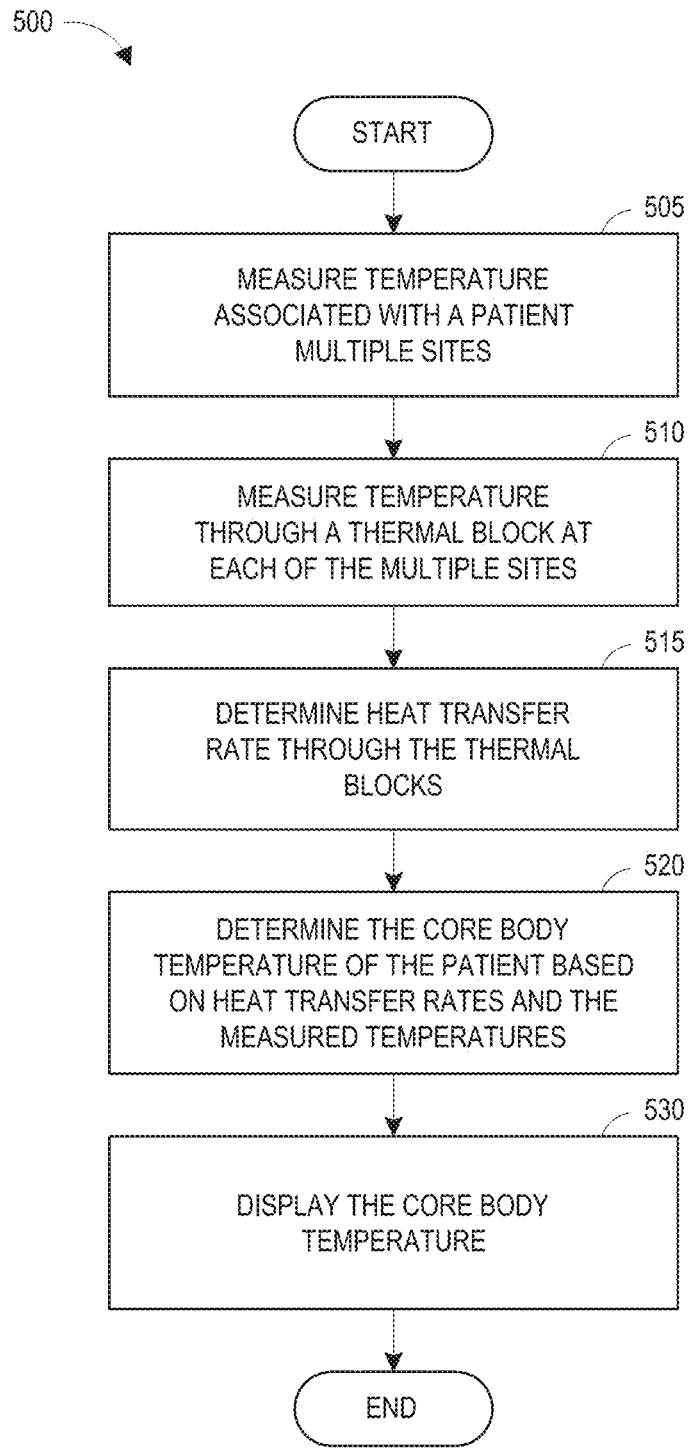
FIG. 5 is a flow diagram illustrating an example process to accurately measure core body temperature using a multi-site temperature monitoring system.

FIG. 5 is a flow diagram 500 illustrating an example process to accurately measure core body temperature using a multi-site temperature monitoring system. The flow diagram 500 can be implemented by the multi-site temperature monitoring system of FIGS. 1, 2, 3, and/or 4.

At block 505, the multi-site temperature monitoring system can measure temperature at multiple locations associated with the surface of the patient. For example, the first temperature measuring device THERM 1 of FIG. 1 can measure the temperature at or near the patient's skin at a first location, and the third temperature measuring device THERM 3 of FIG. 1 can measure the temperature at or near the patient's skin at a second location.

At block 510, the multi-site temperature monitoring system can measure temperature through thermal blocks at multiple sites. For example, the second temperature measuring device THERM 2 of FIG. 1 can measure the temperature through all or at least a portion of the first thermal block Thermal Block 1 at the first location, and the fourth temperature measuring device THERM 4 of FIG. 1 can measure the temperature through all or at least a portion of the second thermal block Thermal Block 2.

At block 515, the multi-site temperature monitoring system can determine the heat transfer rate through the thermal blocks at the multiple sites. For example, the processor 212 of FIG. 2 can receive the temperature measurements, and can use the heat transfer rate equations as described herein to determine the heat transfer rate through the thermal blocks based on the measured temperatures at block 505 and 510, the distance $m_1$ between the first and second temperature measuring devices THERM1, THERM 2, the distance $m_2$ between the third and fourth temperature measuring devices THERM 3, THERM 4, and the thermal conductivities $k_1$, $k_2$.

At block 520, the multi-site temperature monitoring system can determine thermal resistance of the patient's skin and/or the core body temperature of the patient based on the heat transfer rates and measured temperatures. For example, the processor 212 of FIG. 2 can use the core body temperature equations as described herein to determine the core body temperature $T_{CORE}$ of the patient. In other aspects, other equations can be used.

At block 530, the multi-site temperature monitoring system can display the core body temperature of the patient. For example, the multi-site temperature monitoring system can transmit the core body temperature to the display 220 of FIG. 2.

Heat Flux Measurement System

Figure 6A:
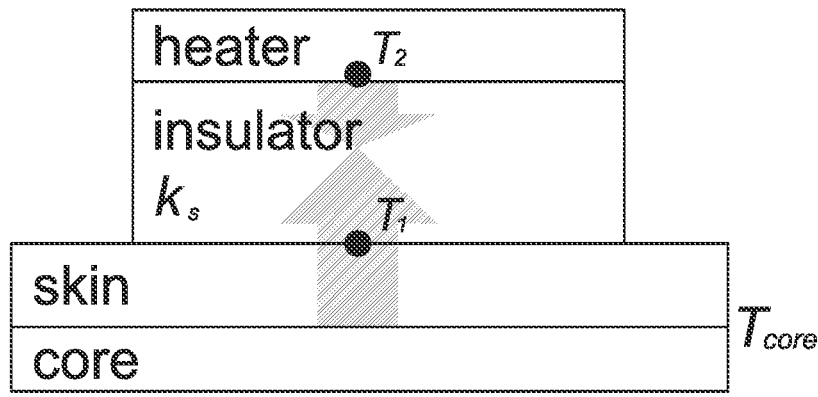
FIG. 6A is a block diagram of an example of an active heat flux measurement system.

FIG. 6A is a block diagram of an example active heat flux measurement system according to certain embodiments. The active heat flux measurement system of FIG. 6A is like the passive heat flux measurement system of FIG. 1A, except the active heat flux measurement system of FIG. 6A can also include a heating component or heater over the insulator and thermistor $T_2$. The heater can be cycled ON and OFF. For example, the active heat flux measurement system of FIG. 6A can further include a controller, such as a PID (proportional-integral-derivative) controller that operates a control loop feedback mechanism. The PID controller can control the heater operation and can repeatedly calculate the difference between the temperature measured at thermistor T1 and thermistor T2. The active heat flux measurement system of FIG. 6A can update the temperature difference measurement and can cycle the heater until thermistor T1 and thermistor T2 have approximately matching values. When the temperatures measured at T1 and T2 can be approximately the same, the net heat flux leaving the body can be approximately equal to the heat flux provided by the heater, and the measured temperature can approximate the core body temperature.

Figure 6B:
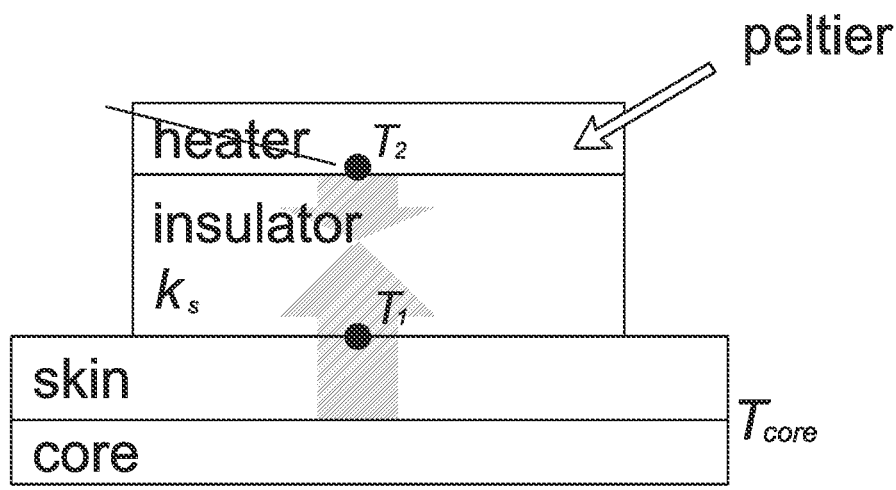
FIG. 6B is a block diagram of an example of another active heat flux measurement system.

FIG. 6B is a block diagram of another example active heat flux measurement system. The active heat flux measurement system of FIG. 6B is like the active heat flux measurement system of FIG. 6A, except that the heater is replaced with a Peltier device. The Peltier effect can be an effect where a heat flux is created (i.e., heat is emitted or absorbed) when an electric current passes across the junction of two different types of materials. A Peltier device, such as a Peltier cooler, heater, or thermoelectric heat pump, can transfer heat from one side of the device to the other, with consumption of electrical energy, depending on the direction of the current. The difference between the active heat flux measurement system of FIG. 6A and the active heat flux measurement system of FIG. 6B, is that in the active heat flux measurement system of FIG. 6B, the Peltier device permits the controller to overheat or under heat the insulator, which impacts the heat flux.

For example, the active heat flux measurement system of FIG. 6B can overheat or under heat to a predetermined temperature and measure the recovery time. The recovery time can provide information about local skin perfusion, which can provide an indication of how the body is regulating temperature.

Figure 6C:
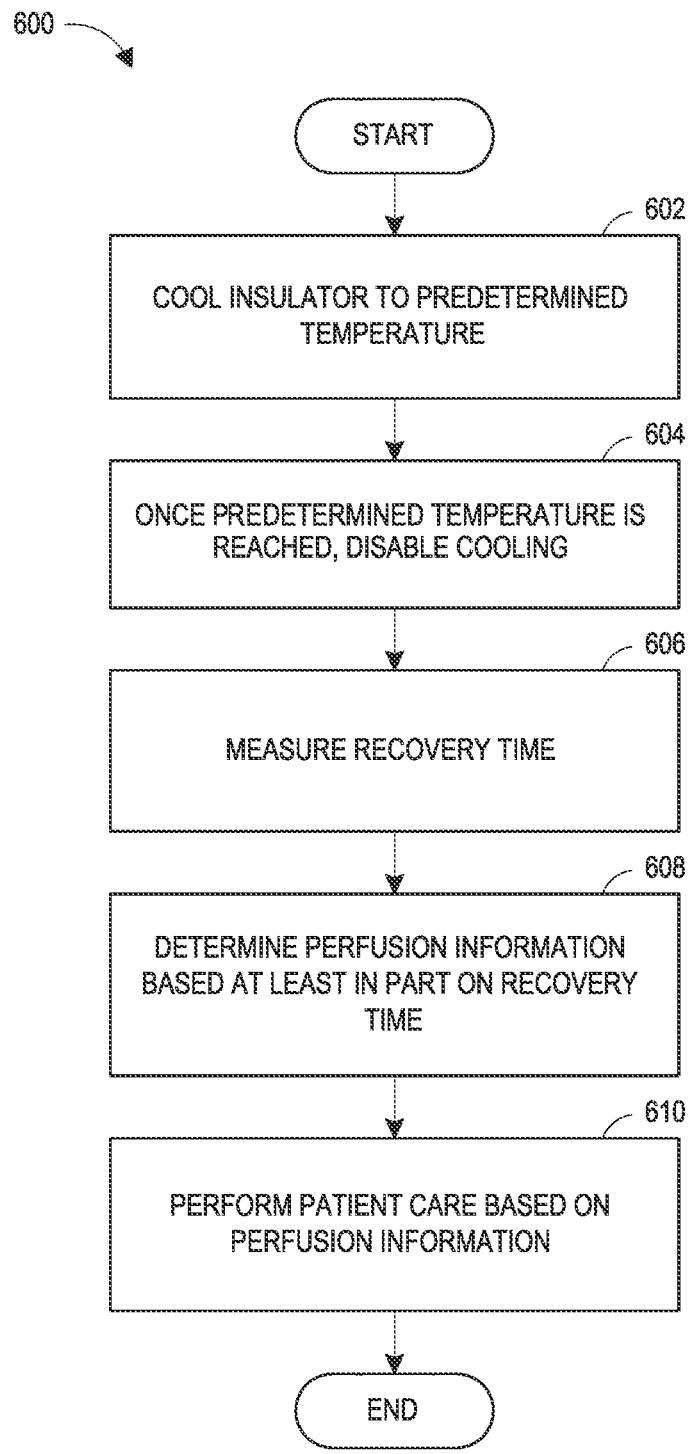
FIG. 6C is a flow chart of an example process to obtain perfusion information of a patient using a Peltier active heat flux measurement system of FIG. 6B.

FIG. 6C is a flow chart of an example process 600 to obtain perfusion information of a patient using a Peltier active heat flux measurement system of FIG. 6B. At block 602, the Peltier device of the Peltier active heat flux measurement system can cool the insulator to a predetermined temperature. The predetermined temperature can be within a few degrees of the patient's skin temperature. The predetermined temperature can be approximately 1 degree less than the patient's skin temperature, approximately 2 degrees less than the patient's skin temperature, approximately 3 degrees less than the patient's skin temperature, approximately 5 degrees less than the patient's skin temperature, and the like. At block 604, the Peltier device can be turned OFF. At block 606, the recovery time between thermistor T1 and thermistor T2 can be measured. At block 608, perfusion information for the patient can be determined based at least in part on one or more of the recovery time, the temperature at thermistor T1 and the temperature at thermistor T2. At block, 610, the caregiver can perform patient care based on the perfusion information.

Terminology

The embodiments disclosed herein are presented by way of examples only and not to limit the scope of the claims that follow. One of ordinary skill in the art will appreciate from the disclosure herein that many variations and modifications can be realized without departing from the scope of the present disclosure.

The term "and/or" herein has its broadest least limiting meaning which is the disclosure includes A alone, B alone, both A and B together, or A or B alternatively, but does not require both A and B or require one of A or one of B. As used herein, the phrase "at least one of" A, B, "and" C should be construed to mean a logical A or B or C, using a non-exclusive logical or.

The description herein is merely illustrative in nature and is in no way intended to limit the disclosure, its application, or uses. For purposes of clarity, the same reference numbers will be used in the drawings to identify similar elements. It should be understood that steps within a method may be executed in different order without altering the principles of the present disclosure.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage. Although the foregoing invention has been described in terms of certain preferred embodiments, other embodiments will be apparent to those of ordinary skill in the art from the disclosure herein. Additionally, other combinations, omissions, substitutions and modifications will be apparent to the skilled artisan in view of the disclosure herein. Accordingly, the present invention is not intended to be limited by the reaction of the preferred embodiments, but is to be defined by reference to claims.

Additionally, all publications, patents, and patent applications mentioned in this specification are herein incorporated by reference to the same extent as if each individual publication, patent, or patent application was specifically and individually indicated to be incorporated by reference.

What is claimed is:

1. A temperature monitoring system comprising:
a first temperature measuring device configured to be disposed at a first location associated with a patient;
a second temperature measuring device;
a first thermal block comprising a first material having a first thermal conductivity and a second material having a second thermal conductivity different than the first thermal conductivity, the first thermal block having a first total thermal conductivity based on at least the first thermal conductivity and the second thermal conductivity, wherein at least a portion of the first thermal block is disposed between the first and second temperature measuring devices, the first temperature measuring device configured to measure a first temperature associated with the patient at the first location, the second temperature measuring device configured to measure a second temperature through the at least the portion of the first thermal block;
a third temperature measuring device configured to be disposed at a second location associated with a patient;
a fourth temperature measuring device;
a second thermal block having a second total thermal conductivity, wherein at least a portion of the second thermal block is disposed between the third and fourth temperature measuring devices, the third temperature measuring device configured to measure a third temperature associated with the patient at the second location, the fourth temperature measuring device configured to measure a fourth temperature through the at least the portion of the second thermal block; and
one or more processors configured to receive temperature measurements from the first, second, third, and fourth temperature measuring devices, and based on the received temperature measurements, the first and second total thermal conductivities, a first distance between the first and second temperature measuring devices, and a second distance between the third and fourth temperature measuring devices, determine a skin thermal resistance of the patient and a core body temperature of the patient, wherein the determined core body temperature is based on at least the determined skin thermal resistance.

2. The system of claim 1 wherein the one or more processors are further configured to determine an ambient air temperature based on at least the received temperature measurements, the first and second thermal conductivities, the first distance between the first and second temperature measuring devices, and the second distance between the third and fourth temperature measuring devices.

3. The system of claim 2 wherein the one or more processors are further configured to refine the determined core body temperature based on at least the determined ambient air temperature.

4. The system of claim 1 wherein the first location is a first surface of the patient's skin, wherein the first temperature measuring device is further configured to measure the first temperature at the first surface of the patient's skin, wherein the second location is a second surface of the patient's skin, and wherein the third temperature measuring device is further configured to measure the third temperature at the second surface of the patient's skin.

5. The system of claim 1 wherein a first side of the first thermal block is over the first location and a first side of the second thermal block is over the second location.

6. The system of claim 5 wherein the second temperature measuring device is configured to measure the second temperature at a second side opposite the first side of the first thermal block and the fourth temperature measuring device is configured to measure the fourth temperature at a second side opposite the first side of the second thermal block.

7. The system of claim 1 wherein at least one of the first, second, third, and fourth temperature measuring devices includes a thermistor.

8. The system of claim 1 further comprising a display configured to display the core body temperature of the patient.

9. The system of claim 1 wherein the first and second distances are approximately the same.

10. The system of claim 1 wherein the first and second thermal conductivities are approximately the same.

11. The system of claim 1 wherein the first and second distances are different.

12. The system of claim 1 wherein the first and second thermal conductivities are different.

13. The system of claim 1 wherein the second thermal block comprises a third material, wherein the first and third materials are the same.

14. The system of claim 1 wherein the second thermal block comprises a third material, wherein the first and third materials are different.

15. The system of claim 1 wherein the first and second distances are approximately the same.

16. The system of claim 1 wherein the first and second total thermal conductivities are different.

17. The system of claim 1 wherein the second thermal block comprises a third material, wherein the third material is different than the first and second materials.

18. A temperature monitoring system comprising:

at least two passive temperature monitoring devices configured to be disposed at respective locations associated with a patient, each passive temperature monitoring device comprising a thermal block between at least portions of first and second temperature measuring devices, at least one of the thermal blocks comprising a plurality of materials, each first temperature measuring device configured to measure a temperature at the respective location, each second temperature measurement device configured to measure a temperature through at least a portion of the corresponding thermal block; and one or more processors configured to determine a skin thermal resistance of the patient and a core body temperature of the patient responsive to the temperature measurements and physical properties associated with the thermal blocks, wherein the determined core body temperature is based on at least the determined skin thermal resistance.

19. The temperature monitoring system of claim 18 wherein the physical properties associated with the thermal blocks include a thermal conductivity and a thickness.

20. The temperature monitoring system of claim 19 wherein, for each passive temperature monitoring device, the thickness of the thermal block represents a distance between the first and second temperature measuring devices.

* * * * *